US012569129B2

(12) United States Patent
Wang et al.

(10) Patent No.: US 12,569,129 B2
(45) Date of Patent: Mar. 10, 2026

(54) ANATOMICAL LOCATION DETECTION OF FEATURES OF A GASTROINTESTINAL TRACT OF A PATIENT

(71) Applicant: Iterative Scopes, Inc., Cambridge, MA (US)

(72) Inventors: Daniel Wang, Cambridge, MA (US); Jonathan Ng, Cambridge, MA (US)

(73) Assignee: Iterative Scopes, Inc., Cambridge, MA (US)

( * ) Notice: Subject to any disclaimer, the term of this patent is extended or adjusted under 35 U.S.C. 154(b) by 539 days.

(21) Appl. No.: 17/990,471

(22) Filed: Nov. 18, 2022

(65) Prior Publication Data

US 2023/0154580 A1     May 18, 2023

Related U.S. Application Data

(60) Provisional application No. 63/280,992, filed on Nov. 18, 2021.

(51) Int. Cl.
G06T 7/10 (2017.01)
A61B 1/00 (2006.01)
(Continued)

(52) U.S. Cl.
CPC .......... A61B 1/31 (2013.01); A61B 1/000094 (2022.02); G06T 7/0016 (2013.01);
(Continued)

(58) Field of Classification Search
USPC ................. 128/920, 922–925; 382/103–107, 382/128–134, 151–159, 162–225;
(Continued)

(56) References Cited

U.S. PATENT DOCUMENTS 7,570,986 B2 *   8/2009   Huang .................. G06T 19/003
                                                              600/407
7,931,588 B2 *   4/2011   Sarvazyan ............... A61B 1/31
                                                              600/117
(Continued)

FOREIGN PATENT DOCUMENTS

CN          104114077 A       10/2014

OTHER PUBLICATIONS

Feng, Jian; Generation Method And System Of Digestive Endoscope Structured Diagnosis Report Based On Image Identification; 2021 (Year: 2021).*

(Continued)

*Primary Examiner* — Marcellus J Augustin
(74) *Attorney, Agent, or Firm* — Fish & Richardson P.C.

(57)          ABSTRACT

Generating a structured medical record from endoscopy data includes obtaining image data including endoscopic images representing portions of a gastrointestinal tract (GI) of a patient; determining features to extract from the image data, the features each representing a physical parameter of the GI tract; extracting the features from the image data; generating anatomical location data specifying a location within the GI tract of a portion of the GI tract represented in the image data; associating the anatomical location data with images that represent the portion of the GI tract; storing, in a node of a data store, data entries including the anatomical location data and the associated one or more images. The data store is configured to receive structured queries for the data entries in the data store and provide the data entries including the transformed features in response to receiving the structured queries.

16 Claims, 6 Drawing Sheets

(51) Int. Cl.

| | | |
|---|---|---|
| *A61B 1/31* | (2006.01) | |
| *G06T 7/00* | (2017.01) | |
| *G06T 17/00* | (2006.01) | |
| *G06T 19/20* | (2011.01) | |

(52) U.S. Cl.
CPC .................. *A61B 1/000096* (2022.02); *G06T 2207/10068* (2013.01); *G06T 2207/20081* (2013.01); *G06T 2207/30032* (2013.01)

(58) Field of Classification Search
USPC ..... 600/300–343, 101–183, 921; 704/1–275; 706/1–62
See application file for complete search history.

(56) References Cited

U.S. PATENT DOCUMENTS

| | | | |
|---|---|---|---|
| 8,131,036 B2 | 3/2012 | Collins et al. | |
| 2008/0117209 A1* | 5/2008 | Razeto | G06T 7/136 |
| | | | 345/424 |
| 2009/0304248 A1* | 12/2009 | Zalis | G06T 7/12 |
| | | | 382/131 |
| 2010/0124365 A1 | 5/2010 | Kanda | |
| 2016/0106347 A1 | 4/2016 | Patwardhan et al. | |
| 2018/0263712 A1* | 9/2018 | Kitamura | A61B 1/00009 |
| 2019/0286652 A1 | 9/2019 | Habbecke et al. | |
| 2020/0364859 A1* | 11/2020 | Najarian | G06N 3/08 |
| 2022/0028550 A1* | 1/2022 | Ng | A61B 5/4848 |
| 2023/0148855 A1 | 5/2023 | Wang et al. | |
| 2024/0112775 A1* | 4/2024 | Madan | G06F 40/205 |
| 2025/0040901 A1* | 2/2025 | Averbuch | A61B 6/5235 |

OTHER PUBLICATIONS

Taniguchi, Katsuyoshi; Image Processing Device And Image Processing Methods; 2014 (Year: 2014).*

Nitsan David; Colonic Cleansing Device; 2008 (Year: 2008).*

Colonic Cleansing Device (Year: 2008).*

Jones Mitchell Lawrence; Localization Systems and Methods for an Ingestible Device; 2018 (Year: 2018).*

Yao et al., "Motion-based camera localization system in colonoscopy videos," Medical Image Analysis, Oct. 2021, 73:102180, 21 pages.

* cited by examiner

400

Obtain image data including endoscopic images representing portions of a
gastrointestinal tract (GI) of a patient                                    402

Determine one or more features to extract from the image data, the
features each representing a physical parameter of the GI tract        404

Extract the one or more features from the image data
406

Generate anatomical location data specifying a location within the GI tract
of at least one portion of the GI tract represented in the image data
408

Associate the anatomical location data with one or more images that
represent the at least one portion of the GI tract                    410

Store, in a node of a data store, one or more data entries including the
anatomical location data and the associated one or more images  412

FIG. 4

ANATOMICAL LOCATION DETECTION OF FEATURES OF A GASTROINTESTINAL TRACT OF A PATIENT

CLAIM OF PRIORITY

This application claims priority under 35 U.S.C. § 119(e) to U.S. Patent Application Ser. No. 63/280,992 filed on Nov. 18, 2021, the entire contents of which are hereby incorporated by reference.

TECHNICAL FIELD

This application relates to image processing. More specifically, this application relates to determining features present in endoscopy images and data to enable subsequent data processing of the endoscopy image and data.

BACKGROUND

An endoscopy refers to a nonsurgical procedure used to examine a patient's digestive tract. Typically, an endoscope, which is a flexible tube that includes a light and camera, is placed within a patient's digestive tract so that a doctor can view images (e.g., still images and/or video) of the patient's digestive tract. For example, during an upper endoscopy, an endoscope is passed through the mouth and throat into the esophagus of a patient, allowing a doctor to view the esophagus, stomach, and upper part of the small intestine. Similarly, an endoscope can be passed into the large intestine of a patient through the rectum to examine this area of the intestine (e.g., a colonoscopy). Endoscopic procedures allow physicians to evaluate several medical conditions, such as causes of stomach pain, appearances of ulcers, bleeding in the digestive tract, and detection of potential malignancies (e.g., polyps). Endoscopic procedures are a key endpoint for healthcare providers to measure IBD outcome and activity. The FDA also increasingly views endoscopic endpoints (as opposed to patient reported symptoms) as a key measure of drug efficacy and performance for IBD related clinical trials.

SUMMARY

This disclosure generally relates to systems and methods for landmark detection in the colon of a patient. Feature data are extracted from the video or image data generated from an endoscopy. A data processing system is configured to detect the features in the images and/or videos from endoscopy data. Based on the detected features, the data processing system is configured to label the endoscopy data with label data specifying anatomical location(s) represented in the respective endoscopy data. The anatomical locations include general segments of the colon (e.g., sigmoid colon, descending colon, transverse colon, ascending colon, etc.). The anatomical locations can include more specific locations within each segment (e.g., cecum within the ascending colon, etc.).

The endoscopy data can include image data, video data, or a combination thereof. For example, video data can be analyzed to predict and determine the anatomical location, such as based on successive frames of the video data. In another example, the data processing system is configured to generate predictions using only discrete image data, such as non-consecutive images or single images of the colon. The data processing system also analyzes metadata included in the endoscopy data. For example, the data processing system can use timestamp data, electronic medical record (EMR) or electronic health record (EHR) data, data from prior endoscopies, and so forth for feature extraction.

The data processing system performs feature extraction in four general stages. A first stage includes data retrieval and pre-processing of retrieved data. A second stage includes several modules, such as machine learning modules, which may work independently or in conjunction to determine an anatomical location in the colon as represented in the endoscopy data. A third stage includes post-processing of outputs of the modules in the second stage. The fourth stage involves documenting these anatomical locations as labels.

The systems and processes described in this document enable one or more of the following technical advantages. The data processing system is configured to label endoscopy data so that the endoscopy data is contextualized for further analysis. The data processing system is configured to generate labeled endoscopy data that can be indexed in a data store. For example, the endoscopy data can be searchable, sortable, and otherwise processed based on the label associated with the endoscopy data. For example, for a downstream data processing of the labeled endoscopy data, a first machine learning model may be applied to the endoscopy data labeled with a first label, while a second, different machine learning model may be applied to the endoscopy data if a second, different label is applied. These labels can also enable rich training datasets for subsequent machine learning applications, drug trials, patient disease prediction and/or tracking, and other such applications.

The systems and methods described in this specification provide one or more of the following advantages for diagnosis and treatment of colonoscopic diseases. The data processing system and processes described in this document enable medical service providers (or other users) to determine an anatomical location of features of interest (such as anomalies) that are discovered in the endoscopy data. Anomalies can include polyps, ulcerations, fissures, and stricturing of the colon that are detected during or after the endoscopy. The association of the malignancy or feature with the anatomical location within the colon improves the continuity of care for patients. For example, the association enables medical service providers to associate a feature detected in a colonoscopy with a feature detected in a separate colonoscopy, enabling the medical service provider to determine whether it is the same feature detected over two different colonoscopies or whether each feature is unique. For example, a physician can determine whether a polyp detected in a second colonoscopy is the same as a polyp detected in a first colonoscopy, or whether the polyp of the second colonoscopy is an entirely new polyp.

In another example, the data processing system enables medical service providers to accurately record which areas of the colon have been identified as having poor bowel preparation (e.g., the ascending colon has solid stool, etc.). Based on the level of bowel preparation in a previous endoscopy, the medical service provider can adjust a prescription of medication that affects preparation of the bowel (e.g., laxatives etc.), such as by increasing a dosage or an amount for the patient. The adjustment can ensure an improved bowel preparation for the patient, and therefore enable an improved clarity of images for future colonoscopies with the patient. In another example, the medical service provider can reduce a prescription of medication to the patient in situations in which the patient shows excellent bowel preparation (e.g., only clear liquids), detected during the colonoscopy. The adjustment improves patient care because the patient experiences a less painful preparation process for future endoscopies. In another example, physicians who conduct future colonoscopies for a patient can take special care when examining locations that were noted to have poor bowel preparation in a previous colonoscopy. This exemplifies how providing the exact anatomical location of these findings can ensure improved patient care.

The data processing system, by providing anatomical location data with the endoscopy data, enables improved diagnosis of certain colonic diseases and may have an impact on the type of medication or treatment options prescribed to the patient, which can improve the quality of care for the patient. For example, for follow-up endoscopies, practitioners can accurately track a disease progression in specific anatomical locations of the patient, enabling an improved continuity of care. Based on the tracked disease progression, a practitioner can determine a patient's response to prescribed medications for colonic diseases and adjust the medication provided. A physician can change a type of medication prescribed, increase or decrease a medication dosage, and so forth, which can improve patient outcomes. In an example, during the performance of a colonoscopy, a practitioner discovers that a patient has mild ulcerative colitis in which inflammation is localized in the rectum and the sigmoid colon (proctosigmoiditis), and the inflammation ends approximately 5 centimeters (cm) away from the rectosigmoid junction. In this example, the practitioner may prescribe topical medication (e.g., 5 ASAs) via suppositories, based on observation of a limited inflammation of the colon, compared to enemas for more extensive inflammation. Continuing this example, in a follow-up colonoscopy, the practitioner discovers that the inflammation has now extended 5 cm above the recto-sigmoid junction. The physician can determine that the patient has not had a positive response to the initial medication prescribed, and topical corticosteroids or oral 5-ASAs may be prescribed. Moreover, the practitioner is able to track the exact disease progression in terms of amount of inflammation in the colon. In another example, a practitioner finds a large number of adenoma polyps within the descending colon, specifically within a small region 5 cm below the splenic flexure and 5 cm above the rectosigmoid junction. A biopsy may indicate that none of these polyps are cancerous, but practitioners who perform follow-up endoscopies on the patient are alerted. These practitioners can be notified to take an elevated care when examining this specific region of the descending colon. The data processing system may label the region as a higher-risk region that has an increased probability for developing colorectal cancer.

In yet another advantage, the anatomical location data, generated by the data processing system and indicating an exact location of features (e.g., anomalies such as polyps) in the colon can reduce the time spent for treatment of patients. The anatomical data enable a reduction of redundant efforts and time elapsing between a diagnosis and providing treatment. For example, when certain polyps are detected and removed during a colonoscopy, polyp tissue is often sent for a biopsy to determine whether it is cancerous. If a specific polyp has been determined to be cancerous, practitioners make an estimation of the exact location of the polyp that needs to be removed via a polypectomy for further testing to determine if the cancer has metastasized. If the practitioner makes an incorrect guess, time is wasted as another surgical procedure will have to be performed. The system and methods described herein removes guesswork and reduces any potential time wasted by documenting an exact location of each polyp.

In yet another advantage, the data processing system, by identifying and documenting exact locations of features such as abnormalities (e.g., stricturing) in the GI tract in a precise location, enables a reduced procedure time for the patient. A physician that is performing a surgery related to the GI tract has the location data generated by the data processing system. The physician can identify exactly when to expect each abnormality and change a procedure strategy or a surgical tool used to traverse the abnormality. For example, if a stricturing of the colon is detected in the descending colon, the stricturing may prevent an endoscope from proceeding past that location in the GI tract. Once the endoscope has been removed, the physician is able to select an endoscopic tool with a smaller diameter that is able to proceed past the identified point. For example, if there is a stricture in the transverse colon, it is important to know the lumen size, the length of the stricture, and the tortuosity of the stricture. These data indicate to a physician which tools to use for advancing past the stricture. If a location of the stricture is not well-defined or is poorly defined, an improper scope (e.g., the endoscope is too large) may be used, or a correct tool may not be available or otherwise prepared in time to re-insert into the colon once the stricture was observed. The precise location data enable the physician to prepare adequately for such abnormalities.

Embodiments of the system and processes that enable one or more of these advantages include at least the following.

In an aspect, a method for automatically generating a structured medical record from endoscopy data includes obtaining image data including endoscopic images representing portions of a gastrointestinal tract (GI) of a patient; determining one or more features to extract from the image data, the features each representing a physical parameter of the GI tract; extracting the one or more features from the image data; based on the features that are extracted, generating anatomical location data specifying a location within the GI tract of at least one portion of the GI tract represented in the image data; associating the anatomical location data with one or more images that represent the at least one portion of the GI tract; and storing, in a node of a data store, one or more data entries including the anatomical location data and the associated one or more images, wherein the data store is configured to receive structured queries for the data entries in the data store and provide the data entries including the transformed features in response to receiving the structured queries.

In some implementations, determining the one or more features comprises: accessing a first machine learning module configured to detect one or more unique features that uniquely identify an anatomical region within the GI tract; detecting, using the first machine learning module, that the one or more unique features are present within the image data; and extracting the one or more unique features from the image data.

In some implementations, determining the one or more features comprises: accessing a second machine learning module configured to detect one or more boundary features indicative of a boundary location between two anatomical regions within the GI tract; detecting, using the second machine learning module, that the one or more boundary features are present within the image data; and extracting the one or more boundary features from the image data.

In some implementations, determining the one or more features comprises: accessing a third machine learning module configured to detecting one or more motion features indicative of a particular motion of an endoscope within the GI tract; detecting, using the third machine learning module, that the one or more motion features are present within the image data; and extracting the one or more motion features from the image data.

In some implementations, the anatomical location data comprises a label indicating an anomaly in the GI tract and a timestamp for video data of the endoscopic data, the timestamp specifying a portion of the video data that represents the anomaly of the GI tract.

In an aspect, a data processing system can include an interface configured to receive video data from a camera, the video data representing a colonoscopy for a patient. The data processing system includes at least one processor configured to perform operations. The operations can be configured to perform process 400. In some implementations, the data processing system is configure to perform operations for alignment of the GI tract to the video data. The operations include obtaining the video data via the interface. The operations include performing coarse alignment of the video data over a time period. The coarse alignment comprises segmenting the video data into segments representing portions of a colon of the patient and assigning a time period to each segment. The operations include performing a medium alignment of the video data based on the coarse alignment. The medium alignment includes determining a motion of the camera through a portion of the colon represented by a segment and determining a location of the camera within the segment for a given time in the time period of the segment. The operations include performing a fine alignment of the video data based on the medium alignment. The fine alignment includes associating one or more features of the colon detected in the segment with a feature time stamp. The operations include generating, from the one or more features of the colon detected based on the fine alignment, structured data representing the colon of the patient. The data processing system includes a user interface configured to present output data representing the structured data.

In some implementations, the structured data comprises a feature vector representing the colon of the patient. The operations further include generating a cluster comprising the feature vector with one or more other feature vectors representing other colons of other patients, the cluster representing patients that have a similar colon disease.

In some implementations, the features comprise one or more of a detected ulceration, a detected erosion, a detected erythema, a detected reduced vascularization, tumors, polyps, a detected friability, or another disease marker.

In some implementations, at least one feature is associated with additional data specifying one or more of a size of the feature, a density of feature in the colon, and an extent of the feature in the colon.

In some implementations, the operations further include performing dimensional grouping of features based on at least one of an anatomical section of the colon or segment of the video data, a frame sequence including the features, and/or a time value associated with one or more of the features.

In some implementations, the operations further include labeling the features, a label specifying at least one of an ileum average size of erosion, an ileum extent of erosions, an ascending colon average ulceration size, an ascending colon erosion density, a transverse colon average ulceration size, a transverse colon erosion density, a descending colon average ulceration size, and a descending colon erosion density.

In some implementations, the video data represent a scope of a colon of the patient including at least one of a cecum, an ileum, and a rectum of the patient.

In some implementations, performing the coarse alignment includes detecting a chronology of features of a path through the colon of the patient, the chronology comprising an ileum, an ascending colon boundary, a transverse colon boundary, a descending colon boundary, and a rectum boundary; and based on the detected chronology, assigning a time stamp to each feature of the path through the colon.

In some implementations, the operations include extracting a set of features from the video data based on a type of disease associated with the video data, wherein the set of features for the video are unique to the type of the disease. The coarse alignment comprises setting at least one boundary based on a feature of the set of features extracted from the video data.

In some implementations, a feature represents a cecal valve, an appendix orifice, or a crow-path pattern of a colon of the patient. In some implementations, a feature represents a colon wall pattern. In some implementations, a feature represents a triangular pattern of a transverse colon. In some implementations, performing the medium alignment comprises detecting a movement type of a camera capturing the video data in the colon. In some implementations, the movement type comprises a hovering the camera in a particular location of the colon. In some implementations, the movement types comprises a quasi-stationary motion of the camera in a location of the colon.

This disclosure incorporates, by reference in entirety, the contents of Patent Application Titled "Systems for Tracking Disease Progression in a Patient," being filed on Nov. 18, 2022, concurrently with this disclosure.

The details of one or more embodiments of these systems and methods are set forth in the accompanying drawings and the description to be presented. Other features, objects, and advantages of these systems and methods are apparent from the description and drawings, and from the claims.

BRIEF DESCRIPTION OF THE DRAWINGS

FIG. 4 shows an example flow diagram for anatomical location detection of features of a gastrointestinal tract of a patient.

DETAILED DESCRIPTION

Figure 1A:
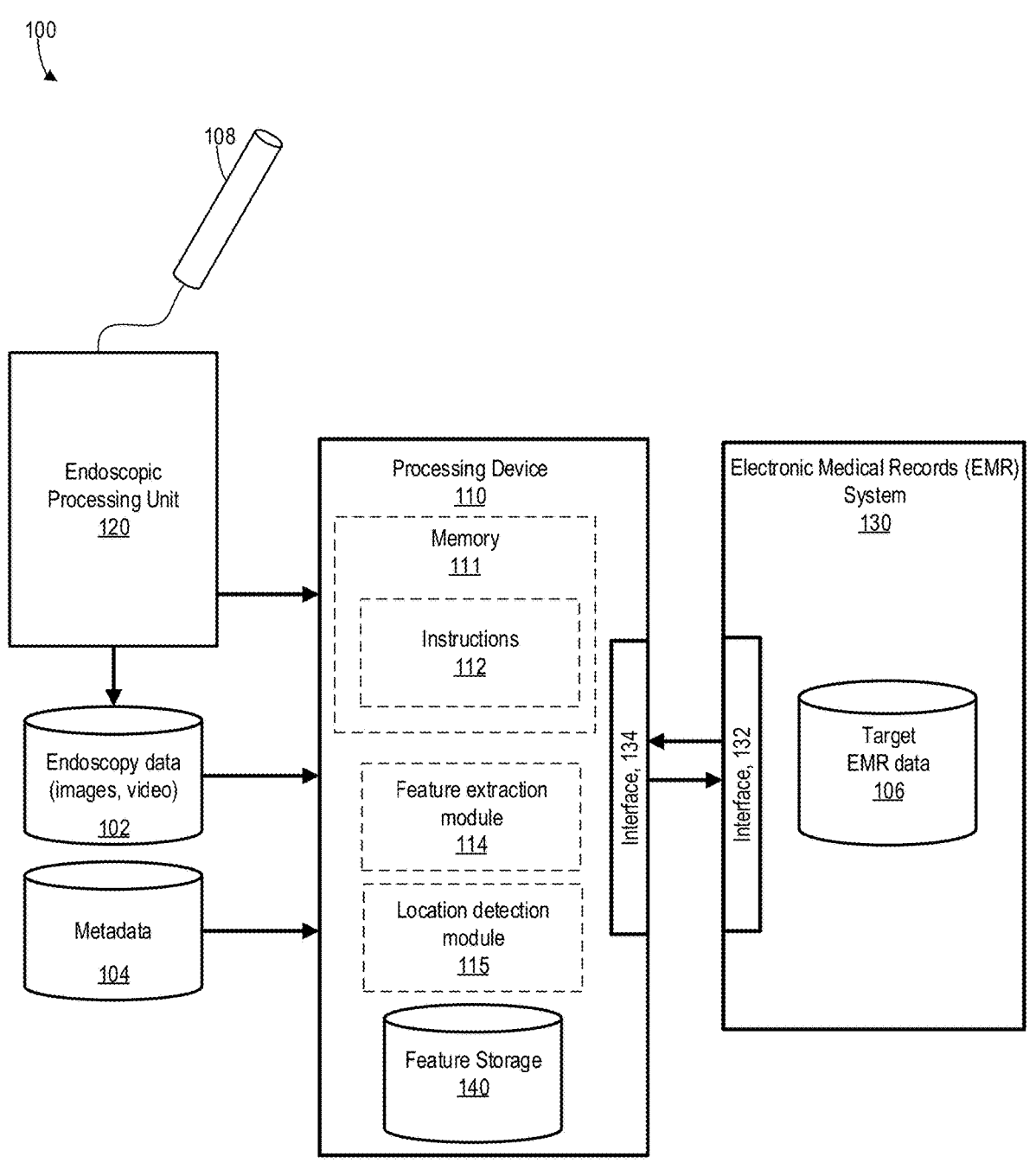
FIG. 1A shows a data processing system for longitudinal alignment of colon videos over multiple time instances for tracking an evolution of a disease.

FIG. 1A shows an example of a data processing system 100 configured to execute one or more processes for automatically generating structured data records, such as electronic medical records, from endoscopy data associated with an endoscopic procedure. The data processing system 100 is configured to receive endoscopy data that includes images and/or video data. The data processing system 100 processes the endoscopy data and extracts features from the endoscopy data. Based on the extracted features, the data processing system 100 is configured to determine a precise location in the GI tract of the patient that is represented in images or video data of the endoscopy data. The precise location is labeled, and the label is stored in a node of the data store with the video or image data that include the precise location. In some implementations, the label is a time stamp that indicates where in a video of the endoscopy a particular feature is represented. In some implementations, the label specifies the precise location and/or GI tract feature represented in an image. The label is a portion of anatomical location data stored in the node with the video and image data for the endoscopy of the patient. In some implementations, each node in the data store is keyed to a patient identifier, and each node stores data entries representing a plurality of endoscopies for the patient.

The structured data records include anatomical location data that specify the precise location of a GI tract represented in images or video acquired during an endoscopy. The precise location can be an exact location in the GI tract of a feature of the GI tract that is represented in the image or video data. A feature of the GI tract can include a unique feature that represents a specific position in the GI tract of the endoscope. A unique feature represents a specific, unique portion of the GI tract. Unique portions of the GI tract can include an appendix, a cecum, an ileocecal valve, an ileum, a *Taenia coli*, a right colic (hepatic) flexure, a left colic (splenic) flexure, a haustra, a sigmoid flexure, a rectum, and an anus.

Generally, the data processing system 100 is configured to generate the anatomical location data and export it to the data store in a series of stages. A first stage includes applying, by the data processing system 100, a single machine learning model or combination of machine learning models to analyze data from the endoscopic processing unit and metadata from a patient. The analysis is described in further detail with respect to FIG. 1B.

A second stage includes applying, by the data processing system 100, a combination of machine learning models that operate either independently or in conjunction with each other to estimate the anatomical location of a GI tract that is represented in an image or frame in a video of the endoscope data 102. The second stage is described in greater detail with respect to FIG. 1C.

A third stage includes performing, by the data processing system 100, a post-processing of the data output by the various machine learning models that are executing in the second stage. For example, when only singular modules are used in the second stage, the third stage is able to post-process the outputs of the module in order to reduce noise in the predictions. The data processing system 100 is configured to use different methods such as smoothing or averaging methods. The data processing system 100 aggregates the results into the form of the final prediction as a singular anatomical location for each frame in the video.

A fourth stage includes generating, by the data processing system, anatomical location data including labels for the images or videos of the endoscopy data 102. The data processing system 100 is configured to export relevant labels into a data store (e.g., a data warehouse) for retrieval by one or more downstream applications. In some implementations, the labels include timestamps for videos. For example, at 1 min 30 s into a given video, the data processing system 100 is able to predict and determine that a splenic flexure is represented in the video. In some implementations, the data processing system 100 compiles the timestamps into a list. Each of these stages is further described below in greater detail.

The data processing system includes a processing device 110, a memory 111 (or a computer readable hardware storage device) configured to host instructions 112, a machine learning module configured to execute one or more trained machine learning platforms, a feature extraction or image processing module 114 to process endoscopy images and/or video, and a location detection module 115. Generally, endoscopy data includes data generated from or associated with an endoscopic procedure and can include video data 102 and associated metadata 104. The data processing system 100 can include an endoscopic processing unit 120 configured to connect to an endoscope 108 for capturing image and/or video data generated by an imaging device of the endoscope 108 during the endoscopy. Instructions can be hosted in either volatile or non-volatile memory, or a combination thereof.

Endoscopy data generally includes all data generated from the imaging device of the endoscope 108 during an endoscopy and subsequent data (such as feature data) generated from the images or video data. The endoscopy data represents the endoscopy and can be analyzed or processed (e.g., by the processing device 110) for generation of the EMR data 106. The endoscopy data 102 are associated with metadata 104 that describe the endoscopy data 102. For example, the metadata 104 includes data/time information, descriptions of the surgical tools being used (such as names or types), a location of the procedure, a name of the physician performing the procedure, and so forth. For example, the data processing system 100 may be able to determine a make and model of the endoscope based on data obtained through the connection to the endoscopic processing unit 120 to the endoscope 108. The metadata 104 can include start time and stop times for a given procedure, and from these data, the processing device 110 determines a duration of the procedure. The metadata 104 may be useful for generating logs or populating portions of the EMR, as subsequently described.

The data processing system 100 is configured to obtain video data 102 from the endoscopic processing unit 120. The endoscopic processing unit 120 includes an imaging device that is configured to capture image data or video data 102. In some implementations, the imaging device is an endoscope 108. The endoscope 108 is an illuminated optical, thin, and tubular instrument (e.g., borescope) used to examine internal organs like the throat or esophagus. The endoscope can be shaped and configured to target specific organs, such as the bladder, kidney, bronchus, colon, and/or pelvis. In some implementations, the endoscope is flexible and includes a camera on one end. The camera can capture image data in the form of still images and/or video. The image or video data 102 can take the form of several data formats, such as RAW, JPEG, PNG, etc. In some implementations, the imaging device includes a digital camera that uses a charge-coupled device (CCD) and/or complementary metal oxide semiconductor (CMOS) to convert photons to electrons for digital processing.

The EMR data 106 includes records associated with individual patients. The EMR data 104 can include self-reported data of the patient. The EMR data 106 can include data obtained from physicians or other medical service providers from interacting with the patient in addition to the data generated automatically by the data processing system 100. For example, the EMR data 106 can include a medical history for the patient, such as medical operations the patient has experienced, illnesses the patient has experienced, and physiological data associated with the patient.

The EMR data 106 generally include a structured record with fields and values in the fields. The EMR data 106 include fields that describe medical aspects of the endoscopy. Different examples of EMR data 106 may include different fields and thus require different combinations of values to be generated by the processing device 110 for populating those fields. For example, a first EMR may include a field for duration of the endoscopy, while a second EMR (e.g., of a different system) may include two fields indicating a start time and a stop time of the endoscopy, but include no field specifying the duration of the procedure. The processing device 110 is configured to determine which fields are included in a given target EMR 106 and populate those fields with the appropriate values automatically. In some implementations, the field may not specify a value acquired directly from the endoscopy data 102 or associated metadata (e.g., start and stop times). Instead, the field may require some additional processing by the processing device 110 to obtain the necessary value, such as calculating a procedure duration from the start and stop times and populating a "duration" field of the target EMR 106 with the duration of the procedure. As such, the processing device 110 is configured to determine what values are specified by fields of the target EMR data 106 and provide the corresponding values. This is described further in relation to FIG. 2.

The EMR data 106 include medical records for particular patients. The EMR data 106 can include data that conform to standard forms. The EMR data 106 can include clinical data for a patient that is provided by a medical service provider in response to a patient visit or telehealth interaction. Generally, the EMR data 106 are on a per-patient basis. This provides a rich history for a particular patient.

The EMR data 106 includes fields and corresponding values representing an endoscopy of a patient in addition to other medical information. The EMR 106 can include a field specifying whether medications are being used by the patient. For example, the EMR data 106 can include whether the patient is using diphenoxylate or opiates as anti-diarrheal medication. The EMR data 106 can include one or more fields specifying demographics data such as age, sex, reproductive history, smoking status, and race or ethnicity of the patient. In another example, one or more fields include values representing data obtained from physically examining the patient by a physician. For example, fields can include a patient medical history which may indicate ileocolonic resection, data indicative of one or more of the presence or absence of an anal fissure, a fistula or abscess, and the presence or absence of one or more complications such as uveitis, pyoderma gangernosum, erythema nodosum, and/or arthralgia. One or more fields of the EMR data can include values representing physicians' global assessment of the patient (e.g., indicating the presence or absence of a condition). The EMR data 106 can include values from pathology laboratory results, such as representing serological profiling results for a time period. The EMR data 106 can include values representing a history of medications prescribed to the patient, including current medications and biologics. The EMR data 106 can include values that represent whether the patient has used biologics. The EMR data 106 can include values that represent disease activity (e.g., whether a disease is active or inactive). The EMR data 106 can include values that represent an IBD type, such as whether the type includes UC or CD. The EMR data 106 can include values that represent a disease duration (e.g., in years). The EMR data 106 can include values that represent a history of surgery for the patient (e.g., whether it has occurred, what surgery has occurred, and when surgery has occurred). The EMR data 106 can include values that represent whether steroid-free remission has occurred. The EMR data 106 can include values that represent fistula drainage (e.g., an extent or occurrence). The EMR data 106 can include values that represent whether the patient has experienced pain or activity restriction (e.g., frequency and severity values associated with either or both). The EMR data 106 can include values that represent a degree of induration for the patient. The EMR data 106 can include values that represent a presence or size of an abdominal mass in the patient. The EMR data 106 can include values that represent whether sexual activity has been restricted. The EMR data 106 can include values that represent a history of flaring (e.g., during a study associated with the patient). The EMR data 106 can include values that represent a hospitalization history for the patient (e.g., time, duration, frequency, etc.). The EMR data 106 can include values that represent a history of thrombosis for the patient (e.g., frequency, location, and/or severity).

In another example, the EMR data 106 can include results from the short IBD questionnaire (e.g., an SIBDQ). These fields can include values representing a patient diet, such as whether dairy has been consumed. The EMR data 106 can include values representing environmental exposures of the patient, including whether over the counter (OTC) drugs have been consumed by the patient, patient infections (e.g., types, locations, frequencies, etc.), and whether the patient has traveled or undergone major life events that may contribute stress to the patient's life. The EMR data 106 can include values representing relevant family history of disease. The EMR data 106 can include values representing fecal incontinence in the patient in the past.

In these examples, the processing device 110 is configured to extract features from the endoscopy data 102 and metadata 104 to determine the anatomical location represented in the images or videos and label the images or portions of the videos with metadata indicating the anatomical locations.

The processing device 110 is configured to receive video or image data 102 from a procedure (e.g., from a colonoscopy). The image or video data 102 generally includes a sequence of frames, each representing a portion of the colon (or other such patient data). A subset of the frames or images of the video or image data 102 can represent symptoms of a disease, such as inflammatory bowel disease (IBD) or other disease. For example, the images can represent bleeding, ulcers or sores, narrowing of the intestines, polyps, and so forth. The processing device 110 is configured to identify the frames or images of the data 102 that represent symptoms using the image processing device 114 (also called a feature extraction module).

The feature extraction module 114 is configured to process the image or video data 102 and other data associated with the endoscopy of the endoscopy data 102 to extract data for populating fields of the target EMR 106. In some implementations, the image processing module 114 is a part of a machine learning module, wherein the image processing module extracts data from the images or videos, and the machine learning module performs classification of the extracted data. For example, the image processing module 114 may perform thresholding operations or feature extraction based on signals received from the machine learning module (e.g., setting threshold values or identifying features in the images to extract).

The feature extraction module 114 can process the images or frames of the video data 102 on an individual basis and/or in combination with one another to identify the presence of IBD symptoms, and so forth). For example, the image processing module 114 can process images frame by frame to identify a symptom presence in the frame by signature matching a region of the image to a known signature representing a symptom). In some implementations, the image processing module 114 is configured to identify where in the image the symptom is manifested and identify, to other modules (such as the machine learning module) which frames or sequence of frames are associated with a symptom.

The feature extraction module 114 generally is configured to tag or identify images or frames as representing a symptom. However, how the image processing module 114 identifies the symptoms can be changed or updated based on feedback from the machine learning module 113. For example, the image processing module 114 can extract image data based on thresholds set or adjusted by the machine learning module. In some implementations, the machine learning module is configured to update, based on training data, image signature data used for classification of the image or video data.

The feature extraction module 114 can process groups of frames or images of video data 102 together. The feature extraction module 114 can be configured to analyze the image in the context of a previous frame (or series of frames) or a subsequent frame (or series of frames). The feature extraction module 114 is configured to facilitate extraction and/or recognition, from image data, of features that are used for populating fields of the target EMR 106. For example, the feature extraction module 114 can facilitate detection of bleeding, polyp formation, etc. by applying one or more feature extraction processes using image processing, and populate an EMR field requesting a list of symptoms, a number of polyps detected, and so forth. Image processing processes can include object detection, pixel thresholding, application of filters to the images or portions of the images, and so forth.

The endoscopy data 102 includes gastro data describing the patient based on the image data received from endoscopy procedures of the patient. The gastro data can include values that represent a location of the endoscopy, such as a lower GI endoscopy. The gastro data can include values that represent a presence of ulcers and/or a number of ulcers. The gastro data can include values that represent a relative vascularity, such as a percentage decrease of vascularity. The gastro data can include values that represent presence of erosions, and a number of the erosions. The gastro data can include values that represent presence or absence of bleeding in the GI tract, and a number of times bleeding was observed (e.g., a number of frames including evidence of bleeding). The gastro data can include values that represent erythema in GI tract). The gastro data can include values that represent a friability (e.g., in GI tract). The gastro data can include values that represent a size of ulcers or erosions. The gastro data can include values that represent a presence of stenosis (e.g., narrowings) of the GI tract. The gastro data can include values that are associated with an upper GI endoscopy (e.g., that specified as located in the upper GI endoscopy data). The gastro data can include values that represent a total ulcerated surface (e.g., presence or absence of this surface, and a percentage of the tract including such a surface). The gastro data can include values that represent a surface affected by disease (e.g., as a percentage of the total surface). The gastro data can include values that represent a disease location in the GI tract. The gastro data can include values that represent a number of lesions observed (e.g., at the case level). The gastro data can include values that represent a presence of cobblestoning in the tract. The gastro data can include values that represent a presence of deep ulcers. The gastro data can include values that represent a type of Crohn's disease observed (e.g., non-stricturing, non-penetrating, stricturing, penetrating, stricturing and penetrating, or perianal). The gastro data can include values that represent a presence of dysplasia in the patient. The gastro data can include values that represent whether activity at a biopsy site is proximal or distal. The features of the image data 102 representing the gastro data are used to populate one or more fields of the target EMR 106 based on the fields identified by the field detection module.

The feature extraction engine 114 is configured to analyze the endoscopy data 102 to extract data describing features of the endoscopy data 102 that is used for determining anatomical locations represented in the endoscopy data (e.g., by location detection module 115). The location detection module uses the features extracted by the module 114 to determine the location for the features (e.g., for anomalies represented by the features). This is described further in relation to FIG. 2, below.

Each feature extracted by the feature extraction module 114 is associated with one or more anatomical locations in the GI tract. The location detection module 115 determines, using the extracted features, a particular portion of the GI tract represented in the images or videos of the endoscopy data 102. Generally, the target EMR 106 is associated with an interface 132 (e.g., an application programming interface or API) of an EMR system 130. The interface 132 provides requirements for the target EMR 106 to the processing device 110.

The computer-readable hardware storage device 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the memory 111 (e.g., computer-readable hardware storage device) includes code-segments (or other executable logic) having executable instructions.

The processing device 110 can be communicatively coupled to the endoscopic processing unit 120 and configured to receive spatially arranged image data (e.g., video data) corresponding with one or more images captured by the imaging device. In some implementations, the processing device 110 includes a general purpose processor. In some implementations, the processing device 110 includes at least one applicable inference processor, accelerated processor which can be utilized in half, single, or double precision (16, 32, or 64 bit floating-point) calculation. The computer processor 110 can also include lots of compute unified device architecture (CUDA) cores, etc., or a combination of thereof. In some implementations, the computer processors 110 include a central processing unit (CPU). In some implementations, the processing device 110 includes at least one application specific integrated circuit (ASIC). The processing device 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The processing device 110 is configured to execute program code means such as the computer-executable instructions 112.

The data processing system can include a display unit (not shown) that is communicatively coupled to the computer processors 110 and configured to show results of the scoring and prediction processes described herein. The display unit can include an electronic display device. In some implementations, the display unit can be configured to act as a touchscreen display device. The display unit is configured to present a user interface. In some implementations, the user interface is a graphical user interface (GUI). The user interface is configured to allow a user of the data processing system 100 to interact with the data processing system 100 through graphical icons and visual indicators. The user interface can use a windows, icons, menus, pointer paradigm (WIMP) to allow a user to interact with the data processing system 100. In some implementations, the user interface cooperates with the endoscopic processing unit 120 to provide a user with a touchscreen GUI. Additionally, or alternatively, the user interface can include one or more input devices such as a mouse and/or keyboard communicatively coupled with the system 100. The user interface can also use a post-WIMP paradigm typically found in touchscreen-based GUIs. In some implementations, the user interface is configured to display images in the form of still photographs and/or videos.

In an embodiment, the processing device 110 is configured to capture features of the endoscopy data 102 and metadata 104 in a stream and provide access to the EMR system 130, without determining any requirements of the EMR system 130 (e.g., without determining a list of fields). For example, the processing device 110 extracts features from the video data 102 and the metadata 104 and stores them in a feature storage 140 which can be accessed by the EMR system 130.

As previously described, types of information can include start/stop times for a procedure, how many polyps were found and one or more characteristics of them. In some implementations, a human in the loop is still included to validate the generated record. Types of data can include when polyps appear and when they disappear in the video. The data processing system 100 is configured to capture images of polyps and potentially upload them to the EMR 106. In some implementations, the data processing system 100 is configured to detect an instrument used during the procedure, such as forceps or a snare. For example, the data processing system 100 is configured to remove a bounding box generated around a polyp when a surgeon is acting on it. The data processing system 100 is configured to detect when in a surgery phase and detect a withdrawal phase of the procedure. The data processing system 100 is trained (e.g., using a machine learning system) to classify polyps and tools in the images.

In some implementations, the data processing system 110 has standardized requirements with regards to information provided to a third party record. These requirements can include a particular format, a range of values, a type of data, and so forth. These requirements will be determined prior to interaction with a third party record requiring the data. For example, specifications made by a healthcare institution or physician may result in a third party record requiring that the data processing system provide particular medical data related to the endoscopy, such as a number of polyps found, a degree or severity of irritation discovered (e.g., on a given scale), or any other relevant information related to the outcome of an endoscopy. These specifications are determined prior to the creation of the data processing system.

In some implementations, data processing system 110 is cloud-based. In some implementations, the data processing system 110 includes a set of distributed computing systems that are networked together. In some implementations, the data processing system 110 includes a single computing system.

In some implementations, to integrate into EMR records, a toolkit is provided to the EMR system 130. Using an API, a function library is provided for accessing particular features extracted from the video data. For example, rather than detect fields of the target EMR 106, the data processing device 110 is configured to provide an output including unstructured text, possibly annotated with keywords. The data processing device 110 captures features and event data during the procedure, and the EMR system 130 can be configured to access the features as needed by requesting them through an interface 134 (e.g., an API). The feature data can be stored in the feature storage 140. In some implementations, the feature storage 140 includes a buffer. The integration can apply to some implementations whereby the EMR system and physicians are able to make specific API calls to request for certain levels of information. For example, a machine learning model can output a set level of detail (high detail, medium detail, low detail). These levels of detail may be changed to improve a processing time, especially for long videos. The level of detail in the output that is provided or requested is a function of editing which output is provided. Generally, a manual edit function is provided for this functionality.

Figure 1B:
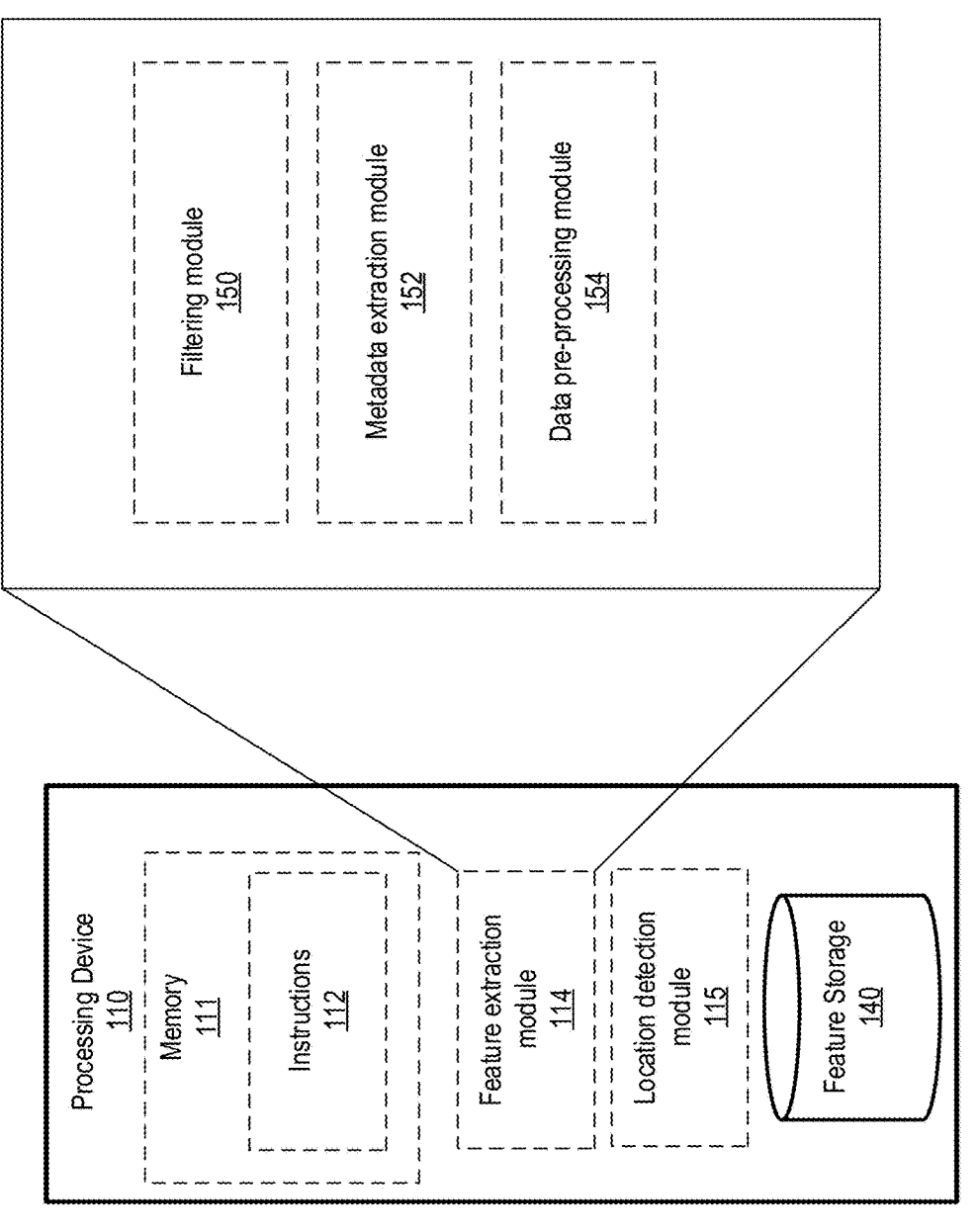
FIG. 1B shows sub-modules of the feature extraction module for performing operations including feature extraction

FIG. 1B shows sub-modules of the feature extraction module for performing operations of the first stage including feature extraction. As previously described, the data processing system 100 is configured to use a single or combination of machine learning models to analyze data from the endoscopic processing unit 120 and metadata 104 from a patient. The data from the endoscopic processing unit 120 may come in the form of images or videos to form endoscopy data 102. In some implementations, only image and/or video data are processed. In some implementations, both image and/or video data and metadata 104 are processed for feature extraction.

A filtering module 150 performs a filtering step. In some implementations, uninformative frames, such as blurry frames, frames with bubbles, frames with a shaky camera, and so forth, are removed from the endoscopy data 102. In some implementations, frames that are uninformative are not filtered from the set of frames. These frames can be retained for processing by certain machine learning modules, but not others. For example, a machine learning module of the data processing device 110 may be retained for establishing baseline data, training the machine learning module, and so forth. In some implementations, these frames are retained for use in machine learning that are capable of using them (e.g., color detection in a blurry frame). One of a plurality of different machine learning filtering algorithms can be selected for filtering out different frames. In some implementations, the filter predictions are transmitted and factored into the machine learning models present in the location detection module 115, but all the frames are still used by the location detection module 115.

A metadata extraction module 152 extracts metadata associated with the frames or images of the endoscopy data 102 that is being analyzed. Metadata 104 includes any EHR/EMR data that could be relevant to the detection of features in the endoscopy data 102. The metadata can include previous surgeries performed on the patient involving the colon, as previously described. For example, metadata regarding previous colectomies performed, indicating which sections of the colon have been removed, is provided if applicable. Metadata 104 also includes start and end times of the procedure in the video data. These metadata are useful to derive a duration of the procedure.

A data pre-processing module 154 prepares the filtered endoscopy data and metadata for input into machine learning modules for location detection. For example, the data processing system 100 can normalize data, weight data, transform data into the appropriate format (e.g., a 1D vector), and so forth.

Figure 1C:
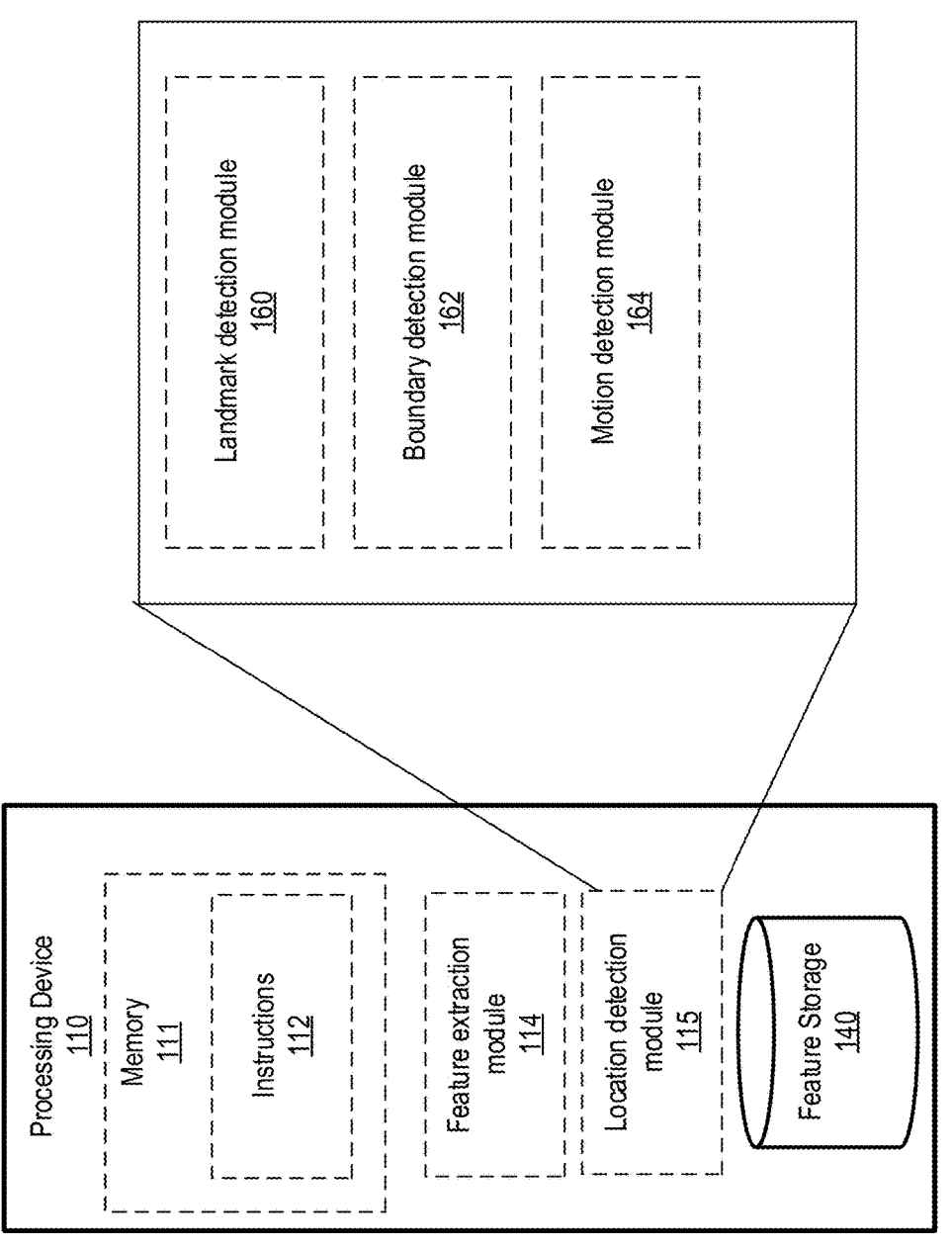
FIG. 1C shows sub-modules for the location detection module including machine learning sub-modules.

FIG. 1C shows sub-modules for the location detection module 115 including machine learning sub-modules. The machine learning sub-modules include a landmark detection module 160, a boundary detection module 162, and a motion detection module 164. These modules 160, 162, and 164 can work independently or in conjunction with each other to estimate the anatomical location of an image or frame in a video. In some implementations, a score is tied to the prediction of the anatomical locations determined by each module 160, 162, 164. This score may be a confidence score that is determined by the machine learning algorithms present in each module. For example, a weighted vote can be performed based on these confidence scores.

The landmark detection module 160 includes logic executed by the data processing system 100 for performing landmark detection within the colon. The landmark detection module 160 is configured to detect unique landmarks within the anatomical locations or regions to determine the broader region or a granular, precise location. The landmark detection module 160 is configured to detect features including one of an appendix, a cecum, an ileocecal valve, an ileum, a *Taenia coli*, a right colic (hepatic) flexure, a left colic (splenic) flexure, a haustra, a sigmoid flexure, a rectum, and an anus. For example, the cecum contains three possible landmarks, including an ileocecal valve, an appendiceal orifice, and Y-shaped "crow's feet" folds. Following this example, the detection of a single landmark, or combination of landmarks within an image or frame within a video, the landmark detection module 160 is able to determine that the anatomical location of this specific image or frame is the cecum.

In some cases, there are no unique landmarks present in a segment of the colon being analyzed in the endoscopy data 102. For example, the transverse and ascending colon are relatively similar and do not have unique anatomical landmarks that differentiate both segments. To assist the landmark detection module 160 to accurately predict the anatomical location without unique landmarks, the boundary detection module 162 is executed.

The boundary detection module 162 includes logic executed by the data processing system 100 for detecting boundaries in the GI tract, including a hepatic flexure, a splenic flexure, a sigmoid-descending colon junction, a rectosigmoid junction, and so forth. The boundaries are located between two segments or anatomical regions of the colon. The boundary detection module 162 is configured to determine the anatomical location of a frame in a video based on a determination if and when in the video (or corresponding image data) a particular boundary is observed. Machine learning model(s) of the boundary detection module 162 are configured to detect any visual indicators within frames within the video that correspond to these boundaries. For example, within a video, boundary detection module 162 determines that both a rectosigmoid junction and a sigmoid-descending colon junction are detected, while a splenic and a hepatic flexure have yet to be detected. Following this example, the metadata of this patient does not show that any part of the colon has been excised as part of a colectomy. As such, the boundary detection module 162 is configured to predict that the frame within the video is located in the descending colon. Such a detection is performed independently from any landmark detection conducted by the landmark detection module 160. This module overcomes the need to detect unique anatomical landmarks for each segment of the colon. However, the outputs of the landmark detection module 160 and the boundary detection module 162 can be combined to increase a confidence value that is lower with application of either individual module independently.

In some implementations, poor bowel preparation or sensor interference (e.g., bubbles etc.) within the images or video frames reduce the quality of the images or video frames of the endoscopy data 102. This noise negatively impacts landmark and/or boundary detection by modules 160, 162, reducing the accuracy of extracting and detecting anatomical landmarks or boundaries between colon segments.

The motion detection module 164 includes logic executed by the data processing system 100 to detect location in the GI tract based on inferred camera motion. The motion detection module 164 functions with less reliance on visual clarity of individual frames, relative to the boundary detection module 162 and landmark detection module 160. Specifically, the motion detection module 164 is a vision-based sensor-free localization system that derives camera motion based on differences within frames. The motion detection module 164 localizes the camera based on the derived motion. In some implementations, the motion detection module 164 is configured to determine an insertion phase and a withdrawal phase of the endoscopic procedure from the derived motion of the camera.

In some implementations, the motion detection module 164 executes a first process to determine the anatomical location. The module 164 compares differences between frames on a longitudinal basis. The module 164 applies a machine learning algorithm to estimate camera motion and therefore determine changes in each of X, Y, and Z dimensions on a three dimensional (3D) plane between consecutive frames. The motion detection module derives a camera trajectory for the entire video. The motion detection module 164 generates a 3D model of the patient's colon. In some implementations, a template 3D model of a colon is used. In some implementations, a unique 3D model of the patient's colon is generated based on image or video data and relevant metadata 104. The motion detection module 164 determines an anatomical location by overlaying the camera trajectory on the 3D colon model.

In some implementations, the motion detection module 164 performs a second process to determine the anatomical location. The motion detection module 164 is configured to derive a camera trajectory from differences between consecutive frames of video data. The module 164 can plot the camera trajectory on a singular dimension. In some implementations, the module 164 plots the camera trajectory on a 3D chart. The module 164 extracts the predictions of segments based on the derived camera trajectory.

As previously stated, a combination of these modules 160, 162, 164 can be used by the location detection module 115 in order to determine the anatomical location of the image or frame. For example, because the motion detection module 164 uses contextual knowledge of frames that occur before and after a relevant portion of the video, (or a segment of the video to analyze motion), the motion detection module 164 is generally used with video data or a sequence or burst of images that are near in time to one another.

In some implementations, the data processing system 100 determines a distance of a detected anomaly from specific landmarks or anatomical locations. The location detection module 115 determines an exact distance (e.g., in centimeters) between the endoscope in the frame and the nearest anatomical landmark or boundary. For example, the location detection module 115 determines that a given frame displayed represents the descending colon at exactly 5 cm away from the splenic junction and 10 cm above the rectosigmoid junction.

The data processing system is configured for post-processing of the location data generated by the location detection module 115. Generally, each individual module 160, 162, 164 generates a portion of the output data that are used for determining a precise location in the GI tract represented by an image or video. Post-processing refers to methods for combining the output data from modules 160, 162, and 164 to predict all of the landmark segments.

When the location extraction module 115 uses multiple modules 160, 162, 164 in conjunction with one another, a machine learning algorithm is applied that filters out noisy or conflicting predictions between the different modules and extracts essential information from each module 160, 162, 164. In some implementations, the location detection module 115 uses extracted essential information from each module 160, 162, 164 to determine a singular anatomical location for a specified image or frame in the video.

The machine learning algorithm is configured to filter out noisy or conflicting predictions between the different modules and extracts essential information from each module. In some implementations, when multiple modules are used in conjunction in the second stage, the data processing device 110, by executing the machine learning algorithm, performs the filtering by averaging multiple, possibly conflicting predictions for the same or otherwise logically related set of frames in order to yield a robust final prediction of landmarks. In an example, different machine learning processes are used as a part of a voting system. Each prediction is weighted with a confidence score, and the prediction having the most weighted votes is selected.

In some implementations, the data processing device 110 performs the filtering by retrieving the confidence score of all the predictions of each module in the second stage. The third stage then uses the confidence scores of the modules, which minimizes the error between the assignments and the model predictions, to determine the most likely assignment of a singular anatomical location for each specified image or frame in the video.

In some implementations, the modules are combined to complement each other by using primarily the most confident predictions of each model. In some implementations, the third stage of this system uses the extracted essential information from each module to determine a singular anatomical location for a specified image or frame in the video.

In some implementations, when the feature extraction module 114 uses multiple modules 150, 152, 154 in conjunction, the location detection module 115 retrieves a confidence score for each of the predictions for each module 150, 152, 154. The location detection module 115 determines a singular anatomical location for each specified image or frame in the video based on applying the module(s) 160, 162, and 164 based on the confidence scores.

In some implementations, when the feature extraction module 114 uses a single sub-module 150, 152, 154, the location detection module 115 post-processes the outputs of that sub-module to reduce noise in the predictions. The location detection module 115 uses one or more smoothing or averaging methods to aggregate the results into the form of the final prediction as a singular anatomical location for each frame in the video.

Returning to FIG. 1A, the data processing system 100 is configured to label the images or videos and/or export the relevant labels into a data store 106 for retrieval at a later stage. In some implementations, the labels will be displayed as timestamps for videos. For example, at 1 min 30 s into a given video, the data processing system 100 is able to predict and determine that a splenic flexure was detected. The data processing system 100 can compile the timestamps into a list.

In some implementations, the data processing system 100 includes a user interface that displays the anatomical location of the image/frame in the video in text format. As a user observes and advances the video, an anatomical location displayed in text adjusts accordingly. In some implementations, the user interface includes a confidence level output by the machine learning model for determining the anatomical location. In some implementations, alternative anatomical location recommendations having lower confidence or accuracy scores are displayed in a separate region of the user interface (e.g., a text box).

In some implementations, the data processing system 100 generates bounding boxes to highlight key anatomical landmarks that resulted in the prediction of the anatomical location. For example, if the data processing system 100 detects a crow's feet anatomical landmark, a bounding box and a text label are generated and dynamically displayed over the landmark in the video. In some implementations, the labels are metadata that are searchable and responsive to data queries of the EMR data 106.

The data processing system 100 is configured to export relevant labels of images and videos into a data warehouse, such as EMR system 130. These data can be retrieved at a later stage or combined with alternative data sources (e.g., information about detection of polyps). In some implementations, the generated anatomical locations data are transcribed into a patient's EMR/EHR directly (e.g., using interface 132/134). In some implementations, the data are stored elsewhere with some association with the image/ series of images or video, such as in a node.

Figure 2:
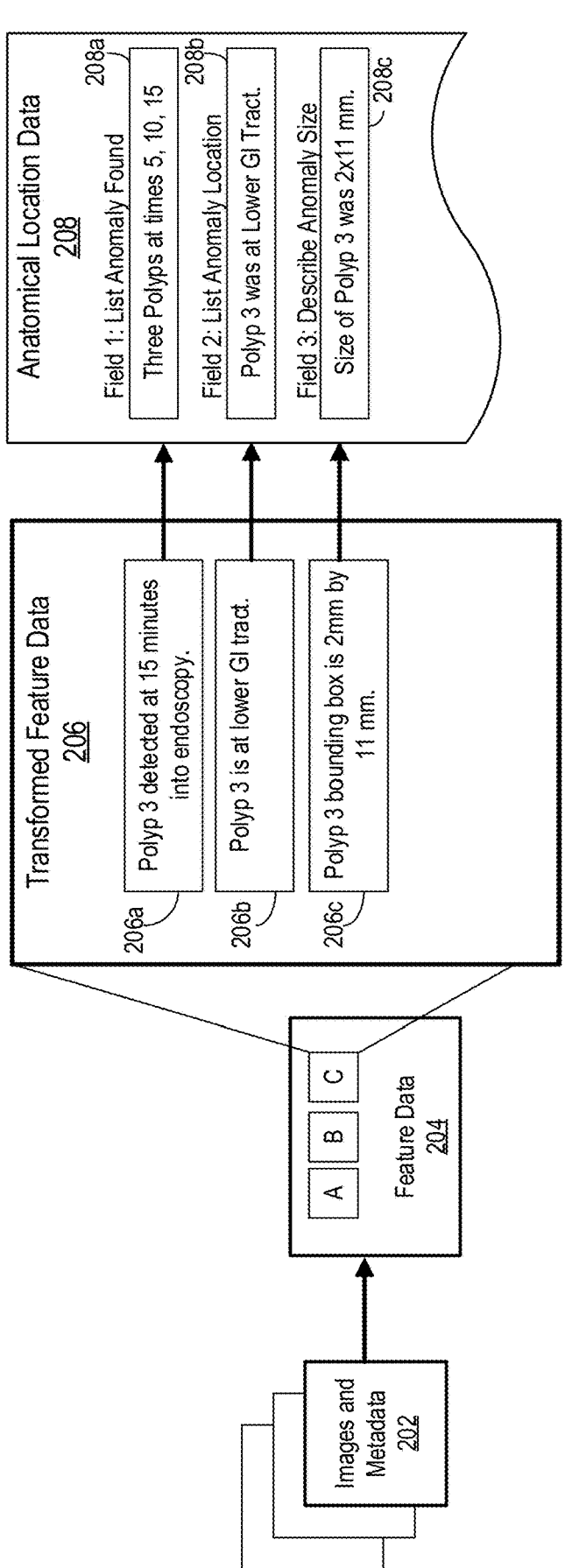
FIG. 2 shows an example of extracting features from the endoscopy data and storing the features in a data store.

FIG. 2 shows an example process for generating anatomical location data from endoscopy data. Generally, the data processing system (e.g., the data processing system 100 of FIG. 1) is configured to intake data for colonoscopy procedure or similar endoscopic procedure. The data processing system 100 is configured to generate anatomical location labels based on images 102 and metadata 104. As shown in FIG. 2, the images and metadata 202 of the endoscopy are transformed into anatomical location data 208.

The images and metadata 202 are received from the endoscopic processing unit 120. The feature extraction module 114 extracts feature data 204 from the video and image data 102 and the metadata 104. Here, the features are represented as blocks "A," "B," and "C." The feature data 204 are generated based on events of the endoscopy, and these features can be combined to generate further data. For example, a start event corresponds to a start time feature, and a stop event corresponds to a stop time feature of the feature data 204. The duration of the procedure can be calculated by combining these two individual features.

As features are detected in the video data (e.g., a polyp is detected), the associated metadata (e.g., time elapsed for that image frame) can be associated with a newly extracted feature representing the polyp. For example, as a series of polyps are detected in the video data 102, each polyp is extracted as a feature (also called an event) of the feature data 204. In FIG. 2, features A, B, and C can each represent a polyp detected in the image data 102. Each feature A, B, and C is associated with other data that are determined from analysis of the video data. For example, for the third polyp (e.g., feature or event "C"), a size value is determined by processing of the images including the third polyp detected. For example, for each video frame including the third polyp "C," a size of the polyp is estimated (e.g., by border detection that is converted to a size based on a known distance from the polyp to the camera or a similar calculation). A series of frames shows the polyp with an average size when viewed from various angles. The processing device 110 stores the size average as feature data which can be used to populate the EMR 208 if requested by the EMR system 130.

Continuing with this example, transformed feature data 206 are generated from the processed image and video data 102 and metadata 104. For feature C, representing a third polyp, a time of detection is stored "Polyp 3 detected at 15 minutes into endoscopy." For feature C, a location is stored "Polyp 3 is at lower GI tract." For feature C, the size of the polyp is stored "Polyp 3 is 2 millimeters (mm) by 11 mm."

Anatomical location data includes fields 1-3 each including respective values 208*a-d* that are generated from the respective transformed features 206*a-c*. Generally, the data included in the EMR 208 are determined based on a query configured by the EMR system 130, as subsequently described. In some implementations, the data processing system 100 is configured to determine what fields are included in EMR 208 and generate corresponding data to satisfy those fields with generated values.

The values 208*a-c* of the respective fields 1-3 of the anatomical location data 208 can be based on the transformed features but need not be identical to the transformed features. In some implementations, features A, B, and C can be directly imported into the anatomical location data 208. The report generated by the data processing system 100 can be formatted based on the query being generated by the EMR system 130. For example, when a size of the polyp is requested, the data processing system 100 can provide a numerical type output, a plain text stream output, and so forth based on the query.

Figure 3:
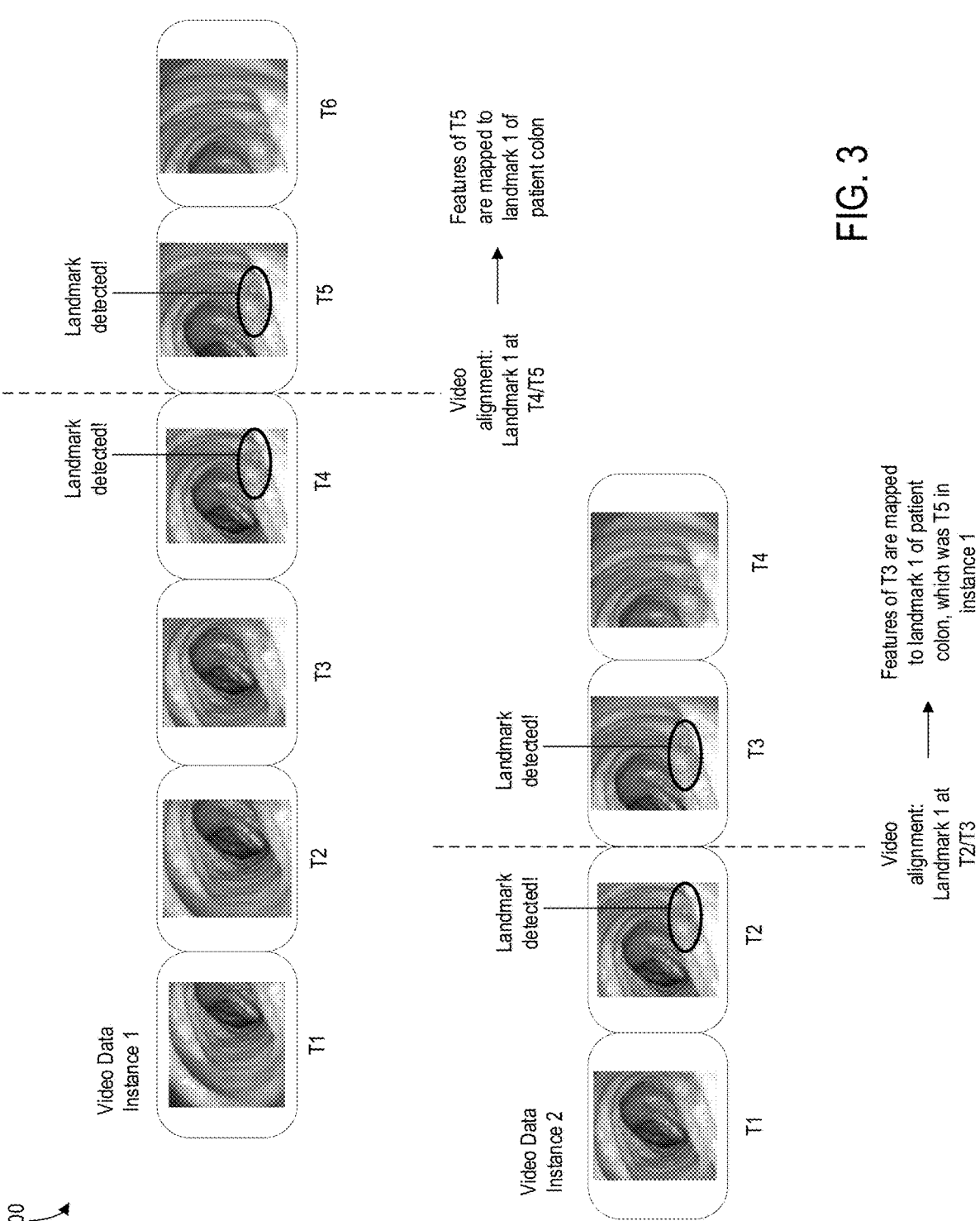
FIG. 3 shows examples of segmenting video data.

FIG. 3 shows an example diagram 300 of longitudinal alignment of colon videos over multiple time instances is performed (e.g., by the data processing system 100 of FIG. 1).

A video recorded of a full colonoscopy from insertion, (an initial time), to full withdrawal, time (an end time). These videos can be screening videos for colorectal cancer detection (CRC) or Irritable Bowel disease (IBD) videos to assess/monitor Ulcerative colitis (UC) or Crohn's diseases (CD) video. These videos will record the entire procedure, insertion of the scope will reach the cecum (CRC, UC) and may proceed to the ileum (UC, CD) and may end with a retroflexion to rectum prior to removal of the scope.

Coarse alignment of video of the same patient over time is performed. Insertion and withdrawal time is variable depending on the physician and findings and the length of the colon is variable depending on each patient. In order to align a recording, the algorithm will first detect boundary landmarks and record the time code (TC). These landmarks are: Cecum detected by recognizing the cecal valve, the appendix orifice or the crow path pattern of the colon; Ileum by detecting its particular colon wall pattern; a transverse colon detected by its characteristic triangular pattern. These are non-disease features.

Given the sequential nature of the video the various time stamps allows the data processing system a recognize which section is represented in the video data currently and allow the data processing system to align these landmarks over the various time points, shown in FIG. 3.

An example chronology of colon features includes the following: an Ileum; a cecum (e.g., alignment landmark is TC_cecum); an ascending colon; an end of the ascending colon and beginning of a transverse colon (e.g., alignment landmark is TC_beg_trans); an end of the transverse colon and beginning of descending colon (e.g., alignment landmark is TC_end_trans); and a rectum (e.g., align landmark is Tc_rectum). At this step the various colon section are anatomically align and time codes are matched/

A medium alignment of the video data for the same patient is performed. Once the segments/sections are aligned, further time based alignment can be performed for further accuracy. An optical flow algorithm can used to detect hovering in a particular spot of the colon, or an image correlation algorithm can be used to detect quasi-stationary motion of the scope. For a given section, the travel time (TT) in the colon is given by: TT=TC_end_section-TC_beg_section-stationary time. A first approximation is performed in which the velocity is constant, so a given motion speed in unit of frames (SpFrame) is given by SpFrame=TT/(number of frame in colon section). Given the SpFrame for a section for 2 videos we can further refine the location of image within a section of the colon.

A fine colon alignment of the video data is performed. Once the approximate location in a given section of the colon is defined, colon features such as hostra can be matched by normalized image, correlation or any known pattern matching techniques, to precisely match specific segments of the colon across different videos.

The data processing system performs feature mapping of the colon. A state of a colon disease such as UC or CD is typically graded using a numerical scale such as the eMS mayo score for UC or SES-CD score for Crohn's disease. The determination of the score depends on specific feature on the colon wall and there is no one-to-one correspondence between scores and underlined featured.

Once longitudinal alignment is achieved and a fine grain score is computed by the data processing system, evolution of the disease can be tracked along the colon from time point to time point. A notable enhancement is to characterize a given location or segment of the colon not by the score but by disease burden, such as by characteristics of the underline features that led to a given score. Typical features include (as previously described): ulceration, erosion, erythema, a reduced vascularization or a loss of vascularization, and friability. The features can be tracked over time and several important characteristics can be computed such as a size of the feature, a density of the feature, or an extent of feature presence. These features can be mapped to the corresponding subsection of the colon and their evolution and attributes tracked over time to assess disease progression, and remission.

Phenotypic characterization of a section of colon is performed by the data processing system. Generally, each of these individual features found along with a given attribute constitutes a separate a feature. In order to reduce dimensionality of the overall feature vector, various section of colon can be grouped together. A typical dimensional grouping of feature can include: by anatomical sections of the colon (e.g., ileum, cecum, ascending, transverse, descending, rectum, etc.); by "alike feature" where frames are sequentially grouped by inventorying the major feature in a frame and extending to sequential frames with the same major feature; and by arbitrarily dividing the color in time based segments. Once an aggregation is defined, and notable characteristics of the feature is decided an endoscopic feature vector is formed and represent a phenotype for the colon. For example such a vector can include ileum average size of erosion, ileum extent of erosions, ascending colon average ulceration size, ascending colon erosion density, a transverse colon average ulceration size, transverse colon erosion density, descending colon average ulceration size, and descending colon erosion density.

In order to facilitate analytical analysis of the phenotype, each entry is normalized in a consistent way. For example, each normalized feature is between 0 and 1 and the feature vector plot can easily be visualized in a radar or spider plot where each spoke is a normalized feature and you can compare evolution over time for a given patient, or patient of a cohort for a given time point. The endoscopic feature vector can be extended to include non-video based data to represent a more extensive phenotype, as described herein. These can include histologic data, PROC data biomarkers, and omics data.

FIG. 4 shows a flow diagram of a process 400 for anatomical location detection of features of a gastrointestinal tract of a patient. The process 400 can be executed by the data processing devices and/or systems described herein, such as data processing device 110 of FIG. 1A.

The process 400 is for automatically generating a structured medical record from endoscopy data. The process 400 includes obtaining (402) image data including endoscopic images representing portions of a gastrointestinal tract (GI) of a patient.

The process 400 includes determining (404) one or more features to extract from the image data, the features each representing a physical parameter of the GI tract. Determining the one or more features can include accessing a first machine learning module configured to detect one or more unique features that uniquely identify an anatomical region within the GI tract. The process 400 includes detecting, using the first machine learning module, that the one or more unique features are present within the image data. The process includes extracting the one or more unique features from the image data. In some implementations, the machine learning modules are trained with endoscopy data from a set of patients, as previously described, for detection of boundary conditions in the GI tract of the patient.

In some implementations, determining the one or more features includes accessing a second machine learning module configured to detect one or more boundary features indicative of a boundary location between two anatomical regions within the GI tract. The process 400 includes detecting, using the second machine learning module, that the one or more boundary features are present within the image data. The process includes extracting the one or more boundary features from the image data.

In some implementations, determining the one or more features includes accessing a third machine learning module configured to detecting one or more motion features indicative of a particular motion of an endoscope within the GI tract. The process 400 includes detecting, using the third machine learning module, that the one or more motion features are present within the image data. The process 400 includes extracting the one or more motion features from the image data.

The process 400 includes extracting (406) the one or more features from the image data. Extracting the one or more features can include detecting that the feature is present in the image data, isolating the feature from other portions of the image data, and determining an identity of the feature in the image data. The extraction can include marking the image data as including the feature (e.g., tagging the image data as including the feature).

The process 400 includes, based on the features that are extracted, generating (408) anatomical location data specifying a location within the GI tract of at least one portion of the GI tract represented in the image data. The process 400 includes associating (410) the anatomical location data with one or more images that represent the at least one portion of the GI tract. The process 400 includes storing (412), in a node of a data store, one or more data entries including the anatomical location data and the associated one or more images, wherein the data store is configured to receive structured queries for the data entries in the data store and provide the data entries including the transformed features in response to receiving the structured queries.

The node of the data store can include a physical, hardware memory location in the data store. The nodes can be connected to structure the data store to respond to the structured queries. For high scale data processing, the structure of the data store reduces a latency of query response. The structure of the data store can be based on types of the features detected, a type of disease represented, and/or patient identifier information. The patient identifier information can be a non-personally identifying information (PII) index, such that the data are anonymized. In some implementations, the structure is based on alignment of the features in the video data to the portions of the video data. This enables quick access to relevant portions of the video data in the data store. For example, for tracking disease development over time, different videos for a patient can be aligned to one another based on detected boundaries in the GI tract for the respective endoscopies.

In some implementations, the anatomical location data includes a label indicating an anomaly in the GI tract and a timestamp for video data of the endoscopic data, the timestamp specifying a portion of the video data that represents the anomaly of the GI tract.

The process 400 can be executed by a data processing system for processing video data representing colonoscopies of a patient. The data processing system can be similar to the data processing device 110 described in relation to FIG. 1A. The data processing system can include an interface configured to receive video data from a camera, the video data representing a colonoscopy for a patient. The data processing system includes at least one processor configured to perform operations. The operations can be configured to perform process 400. In some implementations, the data processing system is configure to perform operations for alignment of the GI tract to the video data. The operations include obtaining the video data via the interface. The operations include performing coarse alignment of the video data over a time period. The coarse alignment comprises segmenting the video data into segments representing portions of a colon of the patient and assigning a time period to each segment. The operations include performing a medium alignment of the video data based on the coarse alignment. The medium alignment includes determining a motion of the camera through a portion of the colon represented by a segment and determining a location of the camera within the segment for a given time in the time period of the segment. The operations include performing a fine alignment of the video data based on the medium alignment. The fine alignment includes associating one or more features of the colon detected in the segment with a feature time stamp. The operations include generating, from the one or more features of the colon detected based on the fine alignment, structured data representing the colon of the patient. The data processing system includes a user interface configured to present output data representing the structured data.

In some implementations, the structured data comprises a feature vector representing the colon of the patient. The operations further include generating a cluster comprising the feature vector with one or more other feature vectors representing other colons of other patients, the cluster representing patients that have a similar colon disease.

In some implementations, the features comprise one or more of a detected ulceration, a detected erosion, a detected erythema, a detected reduced vascularization, tumors, polyps, a detected friability, or another disease marker.

In some implementations, at least one feature is associated with additional data specifying one or more of a size of the feature, a density of feature in the colon, and an extent of the feature in the colon.

In some implementations, the operations further include performing dimensional grouping of features based on at least one of an anatomical section of the colon or segment of the video data, a frame sequence including the features, and/or a time value associated with one or more of the features.

In some implementations, the operations further include labeling the features, a label specifying at least one of an ileum average size of erosion, an ileum extent of erosions, an ascending colon average ulceration size, an ascending colon erosion density, a transverse colon average ulceration size, a transverse colon erosion density, a descending colon average ulceration size, and a descending colon erosion density.

In some implementations, the video data represent a scope of a colon of the patient including at least one of a cecum, an ileum, and a rectum of the patient.

In some implementations, performing the coarse alignment includes detecting a chronology of features of a path through the colon of the patient, the chronology comprising an ileum, an ascending colon boundary, a transverse colon boundary, a descending colon boundary, and a rectum boundary; and based on the detected chronology, assigning a time stamp to each feature of the path through the colon.

In some implementations, the operations include extracting a set of features from the video data based on a type of disease associated with the video data, wherein the set of features for the video are unique to the type of the disease. The coarse alignment comprises setting at least one boundary based on a feature of the set of features extracted from the video data.

In some implementations, a feature represents a cecal valve, an appendix orifice, or a crow-path pattern of a colon of the patient. In some implementations, a feature represents a colon wall pattern. In some implementations, a feature represents a triangular pattern of a transverse colon. In some implementations, performing the medium alignment comprises detecting a movement type of a camera capturing the video data in the colon. In some implementations, the movement type comprises a hovering the camera in a particular location of the colon. In some implementations, the movement types comprises a quasi-stationary motion of the camera in a location of the colon.

In some implementations, a machine learning model includes a convolutional neural network (CNN). A convolutional neural network (CNN) can be configured based on a presumption that inputs to the neural network correspond to image pixel data for an image or other data that includes features at multiple spatial locations. For example, sets of inputs can form a multi-dimensional data structure, such as a tensor, that represent color features of an example digital image (e.g., an image of the surroundings of a vehicle). In some implementations, inputs to the neural network correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the convolutional neural network can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which a system performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R-G-B. A convolutional layer of a neural network of the model computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer.

That is, for each kernel or set of kernels, the model can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The model is configured to compute, when executed by the machine learning module 113, a dot product from the overlapped elements. For example, the model, by the machine learning module 113, is configured to convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The model, by the machine learning module 113 convolves each kernel over each input of an input volume. The model, by the machine learning module 113, performs this convolution operation by, for example, moving (or sliding) each kernel over each input in the region.

The model, by the machine learning module 113, moves each kernel over inputs of the region based on a stride value for a given convolutional layer. For example, when the stride is set to 1, then the model moves the kernels over the region one pixel (or input) at a time. Likewise, when the stride is 2, then the model moves the kernels over the region two pixels at a time. Thus, kernels may be shifted based on a stride value for a layer and the model can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the model produces a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the neural network.

An example convolutional layer can have one or more control parameters for the layer that represent properties of the layer. For example, the control parameters can include a number of kernels, K, the spatial extent of the kernels, F, the stride (or skip), S, and the amount of zero padding, P.

Numerical values for these parameters, the inputs to the layer, and the parameter values of the kernel for the layer shape the computations that occur at the layer and the size of the output volume for the layer. In one implementation, the spatial size of the output volume is computed as a function of the input volume size, W, using the formula (W?F+2P)/S+1. For example, an input tensor can represent a pixel input volume of size [227×227×3]. A convolutional layer of a neural network can have a spatial extent value of F=11, a stride value of S=4, and no zero-padding (P=0). Using the above formula and a layer kernel quantity of K=96, the model performs computations for the layer that results in a convolutional layer output volume of size [55×55×96], where 55 is obtained from [(227−11+0)/4+1=55].

The computations (e.g., dot product computations) for a convolutional layer, or other layers, of a neural network involve performing mathematical operations, e.g., multiplication and addition, using a computation unit of a hardware circuit of the model. The design of a hardware circuit can cause a system to be limited in its ability to fully utilize computing cells of the circuit when performing computations for layers of a neural network.

Based on the aforementioned techniques, the model is configured to identify locations of potential malignancies in images. In some implementations, potential malignancies include polyps. In some implementations, given a set of images, the model is capable of correctly detecting at least 87% of all polyps shown (e.g., at least one image of at least 87% of the polyps presented in the set of images will be correctly detected and identified). In some implementations, when given a set of images, and the model is capable of making a determination that an image does not contain a polyp, and that determination is correct at least 98.7% of the time (e.g., it is likely to be correct 98.7% of the times the machine learning 113 system makes a "does not contain polyp" classification).

In some implementations, the model includes other types of digital neural networks, such as a recurrent neural network (RNN), a radial basis function network, a deconvolution network, a variational auto-encoder (VAE), generative adversarial network (GAN) and so forth.

The data from each of the time points correspond to observations or measurements for a particular patient at a particular region or location (or for a particular symptom). The observations or measurements are associated with one another in the RWS data store, such as with in index or other structured data set. For example, each patient can be represented by a node in structured data set. The node stores an index value representing the patient. The node stores data for each observation or measurement for the patient for each location, symptom, etc. of the patient. The node stores the labels of the anatomical location data and video and/or image data associated with the anatomical data.

While this specification includes many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In some implementations, determining the prediction includes determining one or more frame level annotations corresponding to individual frames of a video of the image data; determining one or more case level annotations for the video of the image data; and determining, based on the one or more frame level annotations and the one or more case level annotations, the score associated with the video of the image data.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and wherein the prediction representing a severity of colon disease in the patient is based on the values of the one or more features.

In some implementations, process includes receiving electronic medical records (EMR) data for the patient, the EMR data including medical information about the patient, wherein the machine learning model is trained with labeled EMR data associating values of medical information of patients with respective severity of colon disease in the patients; extracting one or more values from the EMR data to form an EMR feature vector; processing, by the machine learning model or by a second machine learning model in addition to the machine learning model, the EMR feature vector.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the process includes receiving registry data for the patient, the registry data including patient data across patient populations, wherein the machine learning model is trained with labeled registry data associating values of for patient populations with respective severity of colon disease in particular patients of the patient populations; extracting one or more values from the registry data to form a registry feature vector; processing, by the machine learning model or by a second machine learning model in addition to the machine learning model, the registry feature vector; and generating an updated prediction representing the severity of colon disease in the patient indicated by the registry data or a or treatment recommendation for the patient. In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the process includes receiving omics data for the patient, the omics data including genetic or molecular profiles of patient populations, wherein the machine learning model is trained with labeled omics data associating values of genetic or molecular profiles with respective severity of colon disease in the patients of the patient populations; extracting one or more values from the omics data to form an omics feature vector; processing, by the machine learning model or by a second machine learning model in addition to the machine learning model, the omics feature vector; and generating an updated prediction for the severity of colon disease in the patient indicated by the omics data or a treatment recommendation for the patient.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16 s microbiome sequence from stool of the patient; a 16 s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN) or other models, and wherein the each of the instances of symptoms of colon disease contributes to an activation value for inputting into a layer of the CNN.

In some implementations, processing the feature vector comprises performing a classification with detection bounding boxes and segmentation pixel-wise masks on the image data.

In some implementations, generating the machine learning model includes receiving image data including ground truth scores; labeling the image data; performing frame sampling and score assignment to the frames; applying training data to the machine learning model at a frame level and at a case level; optimizing the machine learning model with validation data at the frame level and the case level; applying test data that is not annotated; and performing case level evaluation of the test data.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

What is claimed is:

1. A data processing system for processing video data representing colonoscopies of a patient, the data processing system comprising:

an interface configured to receive video data from a camera, the video data representing a colonoscopy for a patient;

at least one processor configured to perform operations comprising:

obtaining the video data via the interface;

performing coarse alignment of the video data over a time period, the coarse alignment comprising:

segmenting the video data into segments representing portions of a colon of the patient; and assigning a time period to each segment;

extracting a set of features from the video data based on a type of disease associated with the video data, wherein the set of features for the video are unique to the type of the disease, wherein the coarse alignment comprises setting at least one boundary based on a feature of the set of features extracted from the video data;

performing a medium alignment of the video data based on the coarse alignment, the medium alignment comprising:

determining a motion of the camera through a portion of the colon represented by a segment; and determining a location of the camera within the segment for a given time in the time period of the segment;

performing a fine alignment of the video data based on the medium alignment, the fine alignment comprising:

associating one or more features of the colon detected in the segment with a feature time stamp; and generating, from the one or more features of the colon detected based on the fine alignment, structured data representing the colon of the patient; and a user interface configured to present output data representing the structured data.

2. The data processing system of claim 1, wherein the structured data comprises a feature vector representing the colon of the patient, wherein the operations further comprise:

generating a cluster comprising the feature vector with one or more other feature vectors representing other colons of other patients, the cluster representing patients that have a similar colon disease.

3. The data processing system of claim 1, wherein the features comprise one or more of a detected ulceration, a detected erosion, a detected erythema, a detected reduced vascularization, tumors, polyps, a detected friability, or another disease marker.

4. The data processing system of claim 1, wherein at least one feature is associated with additional data specifying one or more of a size of the feature, a density of feature in the colon, and an extent of the feature in the colon.

5. The data processing system of claim 1, the operations further comprising performing dimensional grouping of features based on at least one of:

an anatomical section of the colon or segment of the video data;

a frame sequence including the features; or a time value associated with one or more of the features.

6. The data processing system of claim 1, the operations further comprising labeling the features, a label specifying at least one of an ileum average size of erosion, an ileum extent of erosions, an ascending colon average ulceration size, an ascending colon erosion density, a transverse colon average ulceration size, a transverse colon erosion density, a descending colon average ulceration size, or a descending colon erosion density.

7. The data processing system of claim 1, wherein the video data represent a scope of a colon of the patient including at least one of a cecum, an ileum, or a rectum of the patient.

8. The data processing system of claim 1, wherein performing the coarse alignment comprises:

detecting a chronology of features of a path through the colon of the patient, the chronology comprising an ileum, an ascending colon boundary, a transverse colon boundary, a descending colon boundary, and a rectum boundary; and based on the detected chronology, assigning a time stamp to each feature of the path through the colon.

9. The data processing system of claim 1, wherein a feature represents a cecal valve, an appendix orifice, or a crow-path pattern of a colon of the patient.

10. The data processing system of claim 1, wherein a feature represents a colon wall pattern.

11. The data processing system of claim 1, wherein a feature represents a triangular pattern of a transverse colon.

12. The data processing system of claim 1, wherein performing the medium alignment comprises detecting a movement type of a camera capturing the video data in the colon.

13. The data processing system of claim 12, wherein the movement type comprises a hovering the camera in a particular location of the colon.

14. The data processing system of claim 12, wherein the movement types comprises a quasi-stationary motion of the camera in a location of the colon.

15. A data processing system for processing video data representing colonoscopies of a patient, the data processing system comprising:

an interface configured to receive video data from a camera, the video data representing a colonoscopy for a patient;

at least one processor configured to perform operations comprising:

obtaining the video data via the interface;

performing coarse alignment of the video data over a time period, the coarse alignment comprising:

segmenting the video data into segments representing portions of a colon of the patient; and assigning a time period to each segment;

performing a medium alignment of the video data based on the coarse alignment, the medium alignment comprising:

determining a motion of the camera through a portion of the colon represented by a segment; and determining a location of the camera within the segment for a given time in the time period of the segment;

performing a fine alignment of the video data based on the medium alignment, the fine alignment comprising:

associating one or more features of the colon detected in the segment with a feature time stamp; and generating, from the one or more features of the colon detected based on the fine alignment, structured data representing the colon of the patient; and a user interface configured to present output data representing the structured data, wherein the structured data comprises a feature vector representing the colon of the patient, wherein the operations further comprise:

generating a cluster comprising the feature vector with one or more other feature vectors representing other colons of other patients, the cluster representing patients that have a similar colon disease.

16. A data processing system for processing video data representing colonoscopies of a patient, the data processing system comprising:

an interface configured to receive video data from a camera, the video data representing a colonoscopy for a patient;

at least one processor configured to perform operations comprising:

obtaining the video data via the interface;

performing coarse alignment of the video data over a time period, the coarse alignment comprising:

segmenting the video data into segments representing portions of a colon of the patient; and assigning a time period to each segment;

extracting a set of features from the video data based on a type of disease associated with the video data, wherein the set of features for the video are unique to the type of the disease, wherein the coarse alignment comprises setting at least one boundary based on a feature of the set of features extracted from the video data;

performing a medium alignment of the video data based on the coarse alignment, the medium alignment comprising:

determining a motion of the camera through a portion of the colon represented by a segment; and determining a location of the camera within the segment for a given time in the time period of the segment;

performing a fine alignment of the video data based on the medium alignment, the fine alignment comprising:

associating one or more features of the colon detected in the segment with a feature time stamp;

labeling the features, a label specifying at least one of an ileum average size of erosion, an ileum extent of erosions, an ascending colon average ulceration size, an ascending colon erosion density, a transverse colon average ulceration size, a transverse colon erosion density, a descending colon average ulceration size, or a descending colon erosion density; and generating, from the one or more features of the colon detected based on the fine alignment, structured data representing the colon of the patient; and a user interface configured to present output data representing the structured data.

* * * * *